United States Patent [19]

Mitchell

[11] 4,180,683

[45] Dec. 25, 1979

[54] PROCESS FOR RECOVERING 2,2-BIS(4-HYDROXYPHENYL)PROPANE FROM DISTILLATION RESIDUES FROM THE PREPARATION THEREOF

[75] Inventor: Lawrence C. Mitchell, Mount Vernon, Ind.

[73] Assignee: General Electric Company, Pittsfield, Mass.

[21] Appl. No.: 863,668

[22] Filed: Dec. 23, 1977

[51] Int. Cl.$^2$ .................. C07C 37/44; C07C 37/38
[52] U.S. Cl. ........................... 568/724; 568/728
[58] Field of Search ......................... 568/724, 728

[56] References Cited

U.S. PATENT DOCUMENTS

| | | | |
|---|---|---|---|
| 2,791,616 | 5/1957 | Luten, Jr. ........................ | 568/728 |
| 2,845,464 | 7/1958 | Luten ............................. | 260/619 |
| 3,073,868 | 1/1963 | Prahl et al. ..................... | 260/619 |
| 3,111,544 | 11/1963 | Joris et al. ..................... | 260/619 |
| 3,162,690 | 12/1964 | Marx et al. ..................... | 260/619 |
| 3,277,183 | 10/1966 | Heller et al. ................... | 260/619 |
| 3,290,390 | 12/1966 | Prahl et al. ..................... | 568/728 |
| 3,290,391 | 12/1966 | Prahl et al. ..................... | 260/619 |
| 3,326,986 | 6/1967 | Dugan et al. .................... | 260/619 |
| 3,359,281 | 12/1967 | Schlichting et al. ............. | 260/345.2 |
| 3,535,389 | 10/1970 | De Jong ......................... | 260/619 |
| 3,627,846 | 12/1971 | Meyer ............................ | 260/619 |
| 3,673,262 | 6/1972 | Prahl et al. ..................... | 260/619 A |
| 3,936,507 | 2/1976 | Ligorati et al. ................. | 260/619 A |
| 3,972,950 | 8/1976 | Kwantes .......................... | 260/619 A |

FOREIGN PATENT DOCUMENTS

| | | |
|---|---|---|
| 147105 | 1/1973 | Czechoslovakia . |
| 971013 | 11/1958 | Fed. Rep. of Germany . |
| 1294664 | 7/1970 | Fed. Rep. of Germany . |
| 1580676 | 9/1969 | France . |
| 45-22539 | 7/1970 | Japan . |
| 45-39251 | 12/1970 | Japan . |
| 48-30269 | 9/1973 | Japan . |
| 57925 | 8/1969 | Poland . |
| 902350 | 8/1962 | United Kingdom ............ 568/724 |
| 1149322 | 4/1969 | United Kingdom ............ 260/619 |

OTHER PUBLICATIONS

Kunoshima Chem. Indust. Co., "C.A." 66:38331j (1967).
Hart et al., "C.A." 67:53879h (1967).
McKay, "C.A." 60:2832C (1963).
Bozovicka et al, "C.A." 60:2832d (1963).
Levkovich et al, "C.A." 55:11370h (1961).

*Primary Examiner*—Norman Morgenstern
*Attorney, Agent, or Firm*—Morgan, Finnegan, Pine, Foley & Lee

[57] ABSTRACT

A process is disclosed for the recovery of 2,2-bis(4-hydroxyphenyl)propane, herein referred to as bisphenol-A, from residues remaining after purification distillation of bisphenol-A produced from a condensation reaction of phenol and acetone. The process comprises mixing the residues with phenol in the absence of acidic reagents to precipitate a bisphenol-A-phenol crystalline adduct and recovering bisphenol-A from the separated adduct.

6 Claims, No Drawings

PROCESS FOR RECOVERING 2,2-BIS(4-HYDROXYPHENYL)PROPANE FROM DISTILLATION RESIDUES FROM THE PREPARATION THEREOF

This invention concerns a process using phenol in the absence of acidic reagents to recover 2,2-bis(4-hydroxyphenyl) propane from residues remaining after purification distillation of 2,2-bis(4-hydroxyphenyl) propane produced from a condensation reaction of phenol and acetone.

BACKGROUND OF THE INVENTION

The use of high purity 2,2-bis(4-hydroxyphenyl) propane, herein referred to as bisphenol-A, as a reactant in the preparation of subsequent formulations such as the preparations of polycarbonate resins is well known in the art. One method for obtaining the purity needed of the bisphenol-A is to distill crude bisphenol-A. In such distillations, a residue is obtained, comprising various by-products and these primarily include higher condensation products of bisphenol-A, condensation products of phenol and acetone produced in the original bisphenol-A formation, colored substances, isomers of bisphenol-A, and the like. Unfortunately, for yield loss purposes, the residues contain 20–60% of bisphenol-A, itself. Prahl et al, U.S. Pat. No. 3,290,390, disclose the addition of phenol to such residues and simultaneously contacting this resulting mixture with an acidic agent such as hydrogen chloride at between room temperature and 150° C. to produce thereform bisphenol-A. However, the method of Prahl et al requires, according to their examples, 16 hours or more reaction time.

It has now been discovered that it is possible to recover the bisphenol-A inherently contained, and in a vastly shorter period of time simply by treating the residue with phenol in the absence of an acidic reagent, such as hydrogen chloride, sulfuric acid, phosphoric acid, and the like. The process of this invention yields bisphenol-A as a solution for subsequent recovery such as by cooling to produce crystals of a 1:1 molar phenol adduct, from which the bisphenol-A can then be recovered, by procedures known per se.

In practice, commercial plants utilize distillation of bisphenol-A as a step in the purification process. The bottoms from the distillation are called "tars" and conventionally these are disposed of by burning. This represents a serious loss in yield because tars contain from 20–60% bisphenol-A plus the isomerizable by-products. Experiments have shown that 28–71% of the bisphenol-A in a typical tar can be recovered by this process. The mother liquor from the crystallization can be stripped of phenol (for recycle) in a separate column, and the diminished quantity of "tar" remaining can be burned or otherwise utilized.

DESCRIPTION OF THE INVENTION

According to the present invention, there is provided a process for the production of 2,2-bis(4-hydroxyphenyl) propane from the tarry residue or isomer by-product residue which remain after purification distillation of 2,2-bis(4-hydroxyphenyl) propane comprising:

(i) forming a warm mixture of said residue and added phenol in the substantial absence of an acidic reagent;

(ii) cooling said mixture to precipitate a crystalline adduct of 2,2-bis(4-hydroxyphenyl) propane and phenol;

(iii) separating the adduct; and (iv) subsequently recovering said 2,2-bis(4-hydroxyphenyl propane therefrom.

The residues contemplated herein are generally referred to as waste streams in commercial purification of bisphenol-A and are many times merely disposed of without treatment to reclaim additional bisphenol-A. In general, the tar by-products comprise (1) higher condensation products of bisphenol-A which are bisphenol-A molecules coupled with themselves and which remain as residue in the purification distillation of bisphenol-A, and (2) isomer by-products, defined as products of phenol and acetone removed with the bisphenol-A fraction during said purification distillation. The tars further include colored substances and various other unknowns.

The ratio of phenol to residue can vary, but that which creates a preferred mixture is about 0.5–2.0:1 and, most preferably, 1.0–1.2:1 by weight.

Although the temperature ranges for steps (i) and (ii) can be varied, preferably, step (i) will be carried out at a temperature between about 60° C. and about 85° C., and step (ii) in a temperature range of from about 20° C. to about 40° C.

The residues with which the process is most efficiently utilized comprise from about 25 to about 50% by weight of bisphenol-A.

Also contemplated is a process wherein step (iv) is carried out by heating said adduct to cause distillation of phenol therefrom and which includes the subsequent step of (v) recycling the phenol back into a reactor for condensation of phenol and acetone.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

EXAMPLE 1

A tarry residue from distillation of a condensation reaction of acetone and phenol, (35 wt.% 2,2-bis(4-hydroxyphenyl) propane), 1500 grams, is heated to an initial temperature of 70° C. and 1500 grams of 70° C. phenol is added (phenol/tar ratio, 1.0/1.0). The mixture is then reduced to a final temperature of 30° C. until formation of a crystalline 1:1 bisphenol-A/phenol molar adduct is substantially complete. Results of gas chromatographic analysis of the adduct thus formed shows 28% of the bisphenol-A present in the completed reaction mixture is present in the adduct formed.

EXAMPLE 2

The procedure of Example 1 is repeated, using phenol in an amount sufficient to provide a phenol/tar ratio of 1.2/1.0. The initial temperature is 75° C.; the final temperature is 35° C. Results of gas chromatographic analysis of the adduct shows 71% of the bisphenol-A present in the completed reaction mixture is present in the adduct formed.

EXAMPLE 3

The procedure of Example 2 is repeated. The initial temperature is 80° C.; the final temperature is 35° C. This time gas chromatographic analysis shows 44% of the bisphenol-A recovered as the adduct.

EXAMPLE 4

A residue comprising isomer by-products from the distillation purification of bisphenol-A made from acetone and phenol (33 wt.% of 2,2-bis(4-hydroxyphenyl) propane), 1500 grams, is heated to an initial temperature of 70° C. and 1500 g of 70° C. phenol is added (phenol/residue ratio, 1.0/1.0). The mixture is then reduced to a final temperature of 30° C. until formation of a crystalline 1:1 bisphenol-A/phenol molar adduct is substantially complete. Results of gas chromatographic analysis of the adduct thus formed shows 51% of the bisphenol-A present in the completed reaction mixture is present in the adduct formed.

Obviously, other modifications and variations of the present invention are possible in light of the above teachings. It is, therefore, to be understood that changes may be made in the particular embodiments of the invention described which are within the full intended scope of the invention as defined by the appended claims.

I claim:

1. A process for the production of 2,2-bis(4-hydroxyphenyl) propane from the tarry residue or isomer by-product residue which remains after purification distillation of 2,2-bis(4-hydroxyphenyl) propane produced by the condensation of phenol and acetone, said process comprising:
    (i) adding phenol to said residue and forming a warm mixture of said residue and added phenol in the substantial absence of an acidic reagent;
    (ii) cooling said mixture to precipitate a crystalline adduct of 2,2-bis(4-hydroxyphenyl) propane and phenol;
    (iii) separating the adduct; and
    (iv) subsequently recovering said 2,2-bis(4-hydroxyphenyl) propane therefrom.

2. A process as defined in claim 1 wherein the warm mixture in step (i) is at a temperature in the range of from about 60° C. to about 85° C.

3. A process as defined in claim 1 wherein cooling step (ii) is in the temperature range of from about 20° C. to about 40° C.

4. A process as defined in claim 1 wherein, in step (i), the amount of phenol comprises from about 0.5 to about 2.0 parts by weight per 1.0 parts by weight of said residue.

5. A process as defined in claim 4 wherein, in step (i), the amount of phenol comprises from about 1.0 to about 1.2 parts by weight per 1.0 parts by weight of said residue and said residue comprises from about 30 to about 40% by weight of 2,2-bis(4-hydroxyphenyl) propane.

6. A process as defined in claim 1 wherein step (iv) is carried out by heating said adduct to cause distillation of phenol therefrom and which includes the subsequent step of
    (v) recycling the phenol back into a reactor for condensation of phenol and acetone.

* * * * *